United States Patent [19]

Fifolt

[11] Patent Number: 4,766,243

[45] Date of Patent: Aug. 23, 1988

[54] ELECTROPHILIC FLUORINATION OF AROMATIC COMPOUNDS

[75] Inventor: Michael J. Fifolt, Grand Island, N.Y.

[73] Assignee: Occidental Chemical Corporation, Niagara Falls, N.Y.

[21] Appl. No.: 639,291

[22] Filed: Aug. 10, 1984

[51] Int. Cl.⁴ .............................................. C07C 85/20
[52] U.S. Cl. ..................... 564/414; 548/476; 558/413; 558/415; 558/423; 564/99; 564/214; 564/218; 564/440; 564/441; 564/442; 568/588; 568/656
[58] Field of Search .................. 564/214, 218, 97, 99, 564/305, 414; 548/476; 260/465 D, 465 E, 465 F; 568/588, 656

[56] References Cited

U.S. PATENT DOCUMENTS

| | | | |
|---|---|---|---|
| 2,689,254 | 9/1954 | Cady | 260/453 |
| 3,420,866 | 1/1969 | Pragen et al. | 260/453 |
| 3,585,218 | 6/1971 | Talbott | 260/350 |
| 3,687,943 | 8/1972 | Barton et al. | 260/239.55 A |
| 3,775,444 | 11/1973 | Jensen et al. | 260/397.6 |
| 3,917,688 | 11/1975 | Barton et al. | 260/543 F |
| 4,030,994 | 6/1977 | Kollonitsch | 204/159.11 |
| 4,532,352 | 1/1985 | Patton | 564/438 |

OTHER PUBLICATIONS

Barton et al, Chem. Soc. London Chem. Comm. (1968), 806–808.
D. Jovanovic, Chem. Abstracts 77:75027n (1972), Fluoroanilides with Antipyretic, Analgesic, Antiinflammatory and Tranquilizing Activity.
Patrick et al, J. Org. Chem. 41,3413 (1976).
Lerman et al., J. Org. Chem. 49,806, (1983).
Lerman et al., J. Org. Chem. 46,4631, (1981).
Kollonitsch et al. J. Am. Chem. Soc. 92,7494 (1970).
Patrick et al. J. Org. Chem., 39,2120 (1974).
Kellogg et al, J. Am. Chem. Soc., 70,3986 (1948).
Allison et al., J. Am. Chem. Soc. 81,1089 (1959).
Barton et al., J. Chem. Soc. Perkins I 739 1974.
Barton et al., J. Am. Chem. Soc., 983034 (1976).
Barton et al., J. Chem. Soc. Perkins I, 712 (1980).
Barton et al., Chemical Communications, 804 (1968).
Thompson, J. Am. Chem. Soc. 89, 1811 (1967).

Primary Examiner—Mary E. Ceperley
Attorney, Agent, or Firm—James F. Tao; Arthur S. Cookfair; James F. Mudd

[57] ABSTRACT

A process for the electrophilic ring fluorination of aromatic compounds which comprises reacting a fluorinating agent from the group consisting of $CF_3OF$ and $CF_2(OF)_2$ with an aromatic compound of the formula

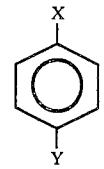

where X is selected from the group consisting of

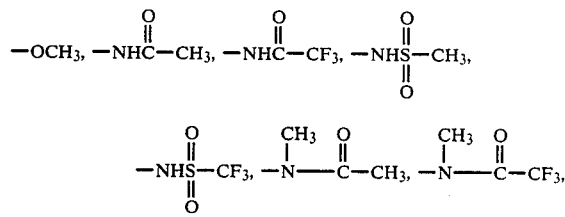

and

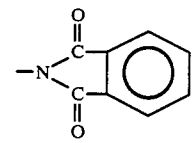

and Y is selected from the group consisting of —H, —CF₃, —CN, —NO₂, —Cl, and CH₃.

1 Claim, No Drawings

ELECTROPHILIC FLUORINATION OF AROMATIC COMPOUNDS

BACKGROUND OF THE INVENTION

This invention relates to a novel process for the electrophilic ring fluorination of aromatic compounds and to novel fluorinated aromatic compounds.

The fluoroxyfluoromethanes utilized as fluorinating agents in the process of this invention include fluoroxytrifluoromethane ($CF_3OF$) and bis-(fluoroxy)-difluoromethane ($CF_2(OF)_2$). The synthesis of fluoroxytrifluoromethane was first disclosed by Kellog and Cady, J. Am. Che. Soc. 70 9386 (1948). See also U.S. Pat. No. 2,689,254 to Cady and Kellogg. The reaction of fluoroxytrifluoromethane with benzene in the vapor phase, catalyzed with a spark or ultraviolet light, has been shown to occur explosively with the production of low yields of fluorobenzene; Allison and Cady, J. Am. Chem. Soc. 81 1089 (1959).

D. H. R. Barton et al. disclosed the reaction of fluoroxytrifluoromethane with saturated hydrocarbons, alkenes, and certain aromatic derivatives, amines and amides; J. Am. Chem. Soc. 98 3034 (1976); J. Chem. Soc. Perkins I 1974, 739; Chemical Communications 1968, 804; J. Chem. Soc. Perkins I, 1980, 712; 1974, 739.

Kollonitsch, U.S. Pat. No. 4,030,994; J. Am. Chem. Soc. 92, 7494 (1970) has disclosed the reaction of certain aromatic substrates under conditions conducive to the formation of free radicals.

The preparation of bis-(fluoroxy)-difluoromethane was first reported by P. G. Thompson; J. Am. Chem. Soc. 89 1811 (1967); and by Prager and Thompson; U.S. Pat. No. 3,420,866. U.S. Pat. No. 3,585,218 to Talbott discloses the reaction of bis-(fluoroxy)difluoromethane with certain aromatic substrates, such as benzene, nitrobenzene, naphthalene, and with pyridine to produce ring fluorinated products.

The ring fluorination of certain aromatic compounds, such as acetanilide, anisole, nitroanisole, dimethoxybenzene, methoxynaphthalene and methyl hydroxybenzoate by reaction with acetyl hypofluorite is disclosed by Lerman, Tor and Rozen; J. Org. Chem. 1981, 46, 4631. The investigation of such reactions involving acetyl hypofluorite with various aromatic substrates is expanded and disclosed in greater detail by Lerman, Tor, Hebel and Rozen in J. Org. Chem. 1984, 49, 806.

The prior art does not indicate that N-substituted anilines will react with fluoroxyfluoromethanes to yield electrophilic aromatic substitution products. In U.S. Pat. No. 3,917,688 to Barton et al, there is disclosed the preparation of N-fluorinated amides and amines on treatment of an acid amide with a hypofluorite including fluoroxytrifluoromethane, indicating that reaction occurs at the nitrogen atom, not on the aromatic ring. Patrick et al., J. Org. Chem. 41 3413 (1976) discloses examples of fluoroxytrifluoromethane undergoing addition reactions with polynuclear aromatic substrates. Barton et al., Chemical Communications 1968, 806, and in U.S. Pat. No. 3,687,943 teaches that the reaction of fluoroxytrifluoromethane with steroids results in the addition of fluorine to the aromatic steroid substrate, in preference to substitution of fluorine on the aromatic ring. In reactions of fluoroxytrifluoromethane with aromatic substrates wherein substitution reactions are indicated, it is taught that conditions conducive to a free radical process are necessary; see U.S. Pat. Nos. 4,030,994 and 3,775,444.

SUMMARY OF THE INVENTION

In accordance with the present invention, there is provided a process for the electrophilic ring fluorination of aromatic compounds which comprises reacting a fluorinating agent from the group consisting of $CF_3OF$ and $CF_2(OF)_2$ with an aromatic compound of the formula

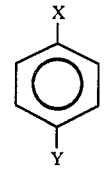

where X is selected from the group consisting of

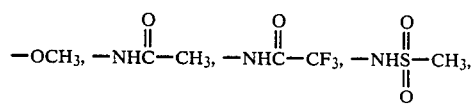

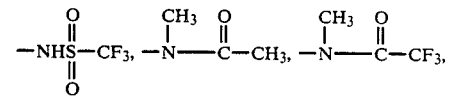

and

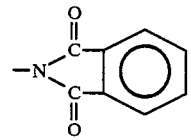

and Y is selected from the group consisting of —H, —$CF_3$, —CN, —$NO_2$, —Cl, and $CH_3$.

In a preferred embodiment the aromatic reactants which may be ring fluorinated in accordance with the invention are N-substituted anilines of the formula

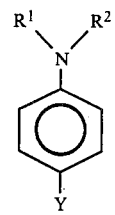

wherein R' is H, $R^2$ is

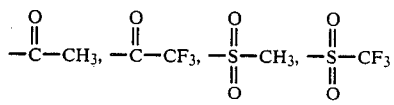

or wherein R' and $R^2$ together represent a phthalimide substituent; and Y is —H, —$CF_3$, —$CH_3$, —$NO_2$, —CN, or Cl. A particularly preferred class of reactants are the acetanilides especially acetanilide and parasubstituted acetanilide such as p-trifluoromethylacetanilide; p-chloroacetanilide; p-cyanoacetanilide; p-nitroacetanilide; p-methylacetanilide; and the like.

The fluorination reactions of this invention may be carried out neat or, preferably, in the presence of a solvent. A wide range of solvents have been found suitable, including for example, aprotic, non-polar solvents such as CHCl₃, CCl₄, CF₃Cl, CH₂Cl₂, and the like; aprotic, polar solvents, such as

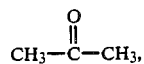

CH₃NO₂, CH₃CN and the like; and protic, polar solvents, including alcohols such as CH₃OH, (CH₃)₃COH, and the like, and carboxylic acids, such as HCO₂H, CH₃CO₂H, CF₃CO₂H and the like. In some reactions, for example, in the fluorination of unsubstituted acetanilide, trifluoroacetanilide, N-phenylmethanesulfonamide or trifluoromethyl-(N-phenyl)-methanesulfonamide, it has been found that the statistical distribution of fluorine atoms on the aromatic ring and, in particular the ortho/para ratio, may vary to some degree depending on the type of solvent employed. If reactivity, at the ortho and para positions were equal, the ratio of ortho to para substituted product would be equal to two on a statistical basis. It has been found, however, that ortho substitution is highly favored, with o/p ratios substantially in excess of 2.0, in an aprotic non-polar solvent, such as CCl₄, while in aprotic polar solvents the ratio is usually less than two. Protic solvents appear to favor the para position. The solvent effect on o/p substitution varies depending on the N-substituted aniline reactant, the most pronounced effect occuring in the fluorination of N-phenylmethanesulfonamide. Data demonstrating this effect is set forth in Table 2, below. From the data shown, it will be seen that it is a particular advantage of this invention that the ortho/para ratio, that is the statistical distribution of fluorine atoms relative to the nitrogen atom may be selectively influenced by selection of solvent and N-substituent.

The reaction is carried out in the liquid phase and the conditions may vary considerably. The reaction may be run at atmospheric pressure, or under superatmospheric pressure under autogenous conditions. The temperature of the reaction may vary considerably, but is typically in the range of about −50° to about 50° Celsius. Lower temperatures may be employed with the practical lower limit being the solidification of the reaction mixture components. The practical upper limit of temperatures for reactions at atmospheric pressure is dependent on the boiling point of reaction mixture components. Still higher temperatures may be employed under conditions or autogenous pressure. The preferred range of reaction temperature is from about −25° to about 30° Celsius.

The fluorinated products obtained in accordance with this invention are typically a mixture of 2-fluoro and 4-fluoro isomers (the latter being formed if the 4-position is available for substitution on the substrate being fluorinated). Some difluoro product may also be formed. (Some difluoro product is typically formed when higher conversions are made, such as 60% or higher).

Most solvents will react to some degree with the fluoroxytrifluoromethane or bis-(fluoroxy)-difluoromethane fluorinating agents. Thus reaction with the solvent may compete to some extent with the reaction with the aromatic substrate. As a result, the selection of a solvent will be based, not only on the solubility of the reactants, but also on the reactivity of the fluorinating agent with the solvent. The ideal solvent, of course, will exhibit high solubility toward the reactants and minimal reactivity with the fluorinating agent. The properties and suitability of a solvent, for this purpose was determined by (A) adding a measured proportion of the fluorinating agent to the solvent; (B) determining the amount of fluorinating agent that passes through the solvent (e.g. by bubbling exit gases through a potassium iodide trap and titrating to find the amount trapped); (C) determining the amount dissolved (e.g. by titration with potassium iodide); and, (D) from that data, calculating the amount of fluorinating agent that reacted with the solvent.

Based on such considerations, the preferred solvents are trifluoroacetic acid, acetic acid, carbon tetrachloride, fluorotrichloromethane, nitromethane, acetonitrile, and chloroform. It will be understood, however, that various other solvents may be employed, if desired, including for example, methylene dichloride, water, fluosulfonic acid, acetone, and the like. It will be appreciated that some solvents may exhibit too high a reactivity to be considered practical for commercial application. For example, it has been found that dimethylformamide and dimethylsulfoxide may react too rapidly for most uses in the process of this invention. Diethylether has been found to react vigorously, with fluoroxytrifluoromethane and thus should be used cautiously, if at all!

The fluorination process of this invention is particularly useful for the preparation of various fluorinated intermediates which, in turn, are useful in the preparation of a wide variety of end products, especially pharmaceutical and agricultural chemicals. For example, the compound 2-fluoro-4-trifluoromethylaniline is known to be a valuable intermediate for the preparation of pesticides. However, prior art methods for the preparation of this intermediate, for example, by conventional fluorination of 4-trifluoromethylaniline have been found inefficient and typically result in the formation of mixtures of polyfluorinated products. The process of this invention provides a new and valuable synthetic route for the preparation of monofluoro aniline compounds by reaction of an aniline derivative, such as an acetanilide with fluoroxytrifluoromethane or bis(-fluoroxy)-difluoromethane to form a fluorinated acetanilide which may, in turn, be conveniently converted, for example, by hydrolysis to form a fluorinated aniline. Thus, for example, the reactant 4-trifluoromethylacetanilide (a novel compound which may be conveniently prepared from 4-trifluoromethylaniline) may be reacted with fluoroxytrifluoromethane or bis-(fluoroxy)-difluoromethane to form 2-fluoro-4-trifluoromethyl acetanilide which may be readily hydrolyzed to form 2-fluoro-4-trifluoromethylaniline. In this process, the N-substituent, in this instance

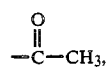

functions as a protecting group, allowing the formation of a mono-fluorinated acetanilide which may be conveniently hydrolyzed to remove the protecting group and yield a fluoroaniline product. This embodiment of the process of this invention is exemplified by the following equation:

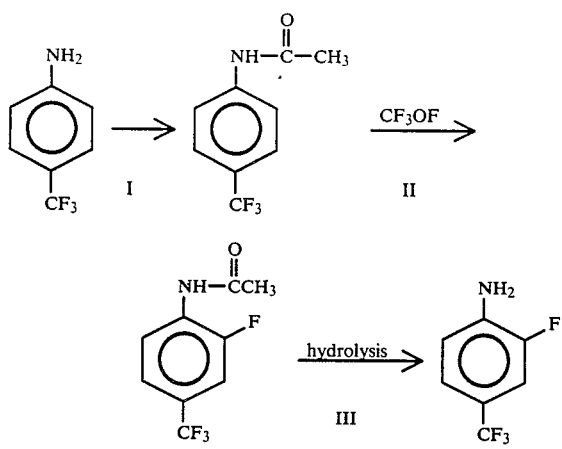

In a similar manner, the fluorination step (II) in accordance with this invention, may be carried out using bis(fluoroxy)difluoromethane as the fluorinating agent in place of fluoroxytrifluoromethane. In place of the N-substituent,

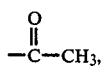

shown in the sequence outlined above, other protecting groups, such as

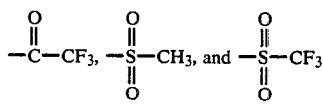

may be employed to protect the amine group from fluorination. Furthermore, a reaction sequence, similar to that exemplified above may be carried out in accordance with this invention, wherein the trifluoromethyl group is replaced by hydrogen or by another electron withdrawing group, such as chloro, nitro, or cyano. The final fluoroaniline product obtained from the hydrolysis step (III) in accordance with this embodiment of the invention, especially at low conversions, will typically contain a substantial portion of the starting aniline reactant. The fluoroaniline product may be recovered by usual physical separation processes such as distillation, fractional crystallization, extraction and the like. In addition, it has been found that the starting aniline and the fluorinated aniline reaction product may be separated by selected precipitation with a mineral acid. Thus, for example, in the embodiment depicted in the above equation, the 2-fluoro-4-trifluoromethylaniline product will typically contain in admixture, a substantial portion of the 4-trifluoromethylaniline reactant. A solution of the crude product, for example, is methylene chloride, may then be acidified with phosphoric acid to cause precipitation of the 4-trifluoromethylaniline as an amine salt which is readily separated by filtration.

The fluorination process of this invention results in the concurrent formation of by-product hydrogen fluoride. If desired, the hydrogen fluoride formed may be neutralized either by treating the effluent gases with a suitable reagent such as an alkali metal hydroxide, for example potassium hydroxide, or by addition of a weak base, such as potassium carbonate to the reaction mixture to neutralize the hydrogen fluoride by in-situ formation of potassium fluoride.

The process of this invention has been found of particular value in the preparation of various useful and heretofore unknown chemical compounds. Among the novel compounds prepared in accordance with this invention are included, for example, N-trifluoroacetyl-2-fluoroaniline; N-trifluoroacetyl-2,4-difluoroaniline; N-trifluoroacetyl-2,6-difluoroaniline; N-(2,4-difluorophenyl)methanesulfonamide; N-(2,6-difluorophenyl)methanesulfonamide; 2-fluoro-4-trifluoromethylacetanilide; and N-(2,4-difluorophenyl)phthalimide. These and other compounds which may be prepared in accordance with the invention make possible a variety of new synthetic routes to the preparation of various pharmaceutical and agricultural chemicals and other useful end products. Thus, the ring fluorinated N-substituted anilines of this invention may be converted, for example, in the manner described in the preceeding paragraph, to fluoranilines. The utility. of fluoroanilines is well known and is disclosed, for example, in U.S. Pat. No. 4,243,819 in the preparation of pesticides.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

Fluorination of Anisole

A solution of 1.08 parts of anisole in 50 parts of chloroform was cooled to about 0° C. and stirred while flubroxytrifluoromethane was added at the rate of about 0.483 parts/hour for about 2.1 hours. The reaction mixture was degassed under reduced pressure and the solvent removed by evaporation on a rotary evaporator. The residue was dissolved in methylene chloride. The solution was washed with water, dried over magnesium sulfate, filtered, and the solvent evaporated to yield 1.84 parts of crude product. Analysis of the crude product by liquid chromatographic techniques indicated 0.213 parts (20%) of unreacted anisole, 0.602 parts (60%) of 2-fluoroanisole and 0.212 parts (20%) of 4-fluoroanisole.

EXAMPLE 2

Preparation of 2-Fluoro-4-chloroacetanilide

A solution of 0.85 parts of 4-chloroacetanilide in 52 parts of acetic acid was cooled to 0° C. and stirred while 0.542 parts of fluoroxytrifluoromethane was added over a period of one hour. The reaction mixture was degassed and the solvent removed reduced pressure. Analysis of the remaining crude reaction product by gas chromatographic techniques indicated a 60% yield of 2-fluoro-4-chloro-acetanilide and a 5% yield of 2,6-difluoroacetanilide at 83% conversion.

EXAMPLE 3

Fluorination of N-trifluoroacetylaniline

A solution of 9.5 parts of N-trifluoroacetylaniline in 740 parts of chloroform was cooled to 0° C. and fluoroxytrifluoromethane was added at a rate of 4.31 parts/hr for 2 hours. Gas chromatographic analysis of the reaction product indicated 4% unreated N-trifluoroacetylaniline, 44% N-trifluoroacetyl-2-fluoroaniline, 11% N-trifluoroacetyl-4-fluoroaniline, 3% N-trifluoroacetyl-2,4-di-fluoroaniline, 8% N-trifluoroacetyl-2,6-difluoroaniline, and 1% N-trifluoroacetyl-2,4,6-trifluoroaniline.

EXAMPLE 4

Fluorination of acetanilide

A solution of 67.5 parts of acetanilide in 22,200 parts of chloroform was cooled to 0° C. and maintained at that temperature for 2.5 hours while fluoroxytrifluoromethane was bubbled into the solution at a rate of 46 parts per hour. Analysis of the reaction product by gas chromatographic technique indicated a 91 percent conversion with a yield of 37% 2-fluoroacetanilide, 16% 4-fluoroacetanilide, 10% 2,4-difluoroacetanilide, 3% 2,6-difluoroacetanilide and about 25% higher molecular weight material.

EXAMPLE 5–24

Fluorination of acetanilide

Following the general procedure of the preceeding examples acetanilide (135 parts) was reacted with fluoroxytrifluoromethane (FTM) or bis-(fluoroxy)-difluoromethane (BDM) in a series of reactions in various solvents and under various conditions with the results as set forth in Table I, below. The fluorinations were carried out at low conversions to minimize formation of difluoro products and to obtain accurate data relative to ortho/para ratio of product.

parts of white solid. The filtrate was evaporated to yield 12.8 parts of white solid. The solids were combined and the recrystallization and concentration processes were repeated several times to yield 22.7 parts 4-trifluoromethylacetanilide (82% yield), melting point 152°–153.5° C.

(B) Preparation of 2-Fluoro-4-trifluoromethylacetanilide

A solution of 20 parts of 4-trifluoromethylacetanilide in 74 parts of acetic acid was cooled to about 0° C. and maintained at that temperature while 18.4 parts of fluoroxytrifluoromethane was added over an eight hour period. The reaction mixture was then degassed and the solvent removed with a rotary evaporator. The remaining solid was dissolved in chloroform, washed with water and dried by evaporation. Analysis by column chromatography indicate a yield of 8.7 parts of pure 2-fluoro-4-trifluoromethylacetanilide, melting point 135°–7° C.

(C) Hydrolysis to 2-fluoroaniline

A solution of 5.5 parts of 2-fluoro-4-trifluoromethylacetanilide in 41 parts of ethanol was heated to reflux and 14.9 parts of concentrated hydrochloric acid was added. After one hour the reaction mixture was allowed to cool and a white precipitate formed. The solvent was removed under reduced pressure and the remaining crude product was dissolved in water, treated with sodium bicarbonate, extracted with methylene chloride, dried and evaporated to remove the methylene chloride solvent. The remaining product was

TABLE 1

| | | | Fluorination of Acetanilide | | | | | |
|---|---|---|---|---|---|---|---|---|
| | | | | Reaction Mixture Analysis (%) | | | | |
| Example No. | | Solvent (parts) | | Temperature (°C.) | Unreacted Acetanilide | 2-Fluoro-Acetanilide | 4-Fluoro-Acetanilide | 2,4- & 2,6-Di-Fluoroacetanilide | Ortho/para |
| | FTM (parts) | | | | | | | | |
| 5 | 41.6 | CH$_2$Cl$_2$ | 13,400 | 23 | 76 | 12 | 6 | 0.5 | 2.0 |
| 6 | 20.8 | CH$_3$NO$_2$ | 11,400 | 24 | 85 | 9 | 4 | 0.7 | 1.9 |
| 7 | 26 | CH$_3$Cl | 14,900 | 23 | 75 | 13 | 6 | 0.4 | 2.2 |
| 8 | 20.8 | CH$_3$COOH | 10,500 | 23 | 83 | 8 | 4 | 0.6 | 2.0 |
| 9 | 26 | CCl$_4$ | 15,900 | 24 | 76 | 11 | 4 | — | 2.8 |
| 10 | 36.4 | (CH$_3$)$_3$COH | 7,819 | 27 | 77 | 10 | 5 | 0.9 | 2.0 |
| 11 | 93.6 | CH$_3$COCH$_3$ | 7,920 | 24 | 38 | 34 | 16 | 4.8 | 2.1 |
| 12 | 156 | CH$_3$COCH$_3$ | 7,920 | 24 | 7 | 40 | 16 | 16 | 2.5 |
| 13 | 20.8 | CH$_3$COCH$_3$ | 7,920 | −25 | 84 | 9 | 5 | 0.1 | 1.8 |
| 14 | 20.8 | CH$_3$COCH$_3$ | 7,920 | 0 | 82 | 9 | 5 | 0.1 | 1.8 |
| 15 | 20.8 | CH$_3$COCH$_3$ | 7,920 | 50 | 85 | 7 | 5 | 0.1 | 1.4 |
| | BDM (parts) | | | | | | | | |
| 16 | 15.0 | CCl$_4$ | 180,000 | 25 | 77 | 10 | 2 | 0.7 | 5.0 |
| 17 | 12.0 | CH$_3$CN | 7,830 | 23 | 84 | 7 | 3 | 0.4 | 2.3 |
| 18 | 24.0 | CF$_3$COOH | 15,400 | 24 | 71 | 20 | 6 | 0.7 | 3.3 |
| 19 | 15.0 | HCOOH | 12,200 | 24 | 81 | 9 | 4 | 1.1 | 2.3 |
| 20 | 15.0 | CH$_3$COCH$_3$ | 7,920 | −25 | 77 | 10 | 5 | 1.4 | 3.6 |
| 21 | 15.0 | CH$_3$COCH$_3$ | 7,920 | 0 | 77 | 10 | 5 | 1.4 | 3.6 |
| 22 | 15.0 | CH$_3$COCH$_3$ | 7,920 | 24 | 81 | 9 | 4 | 1.1 | 3.6 |
| 23 | 15.0 | CH$_3$COCH$_3$ | 7,920 | 50 | 76 | 10 | 5 | 0.6 | 2.0 |
| 24 | 90.0 | CH$_3$COCH$_3$ | 7,920 | 24 | 12 | 29 | 10 | 16 | 2.9 |

EXAMPLE 25

Preparation of 2-fluoro-4-trifluoromethylaniline (A) Preparation of 4-trifluoromethylacetanilide A solution of 20.5 parts of 4-trifluoromethylaniline in 119 parts of chloroform was maintained at about 24° C. with stirring while 25.97 parts of acetic anhydride was added over a period of two hours. The precipitate which formed was filtered and washed to yield 16.35 distilled at 55° C. (0.3 torr) to yield 3.97 parts of 2-fluoro-4-trifluoromethylaniline. The structure of the final product was confirmed by C-13 nuclear nagnetic resonance in comparison with a known sample.

EXAMPLE 26

Preparation of 2-fluoro-4-trifluoromethylaniline

A solution of 10 parts of 4-trifluoromethylacetanilide in 60 parts of acetic acid was maintained at about 29° C. (with stirring over a period of seven hours) while fluoroxytrifluoromethane was added at a rate of about one part per hour. The acetic acid was then removed by distillation under reduced pressure. The crude reaction product was dissolved in chloroform, washed three times with water, dried over anhydrous magnesium sulfate, filtered, and the chloroform removed by distillation at reduced pressure to yield 11.07 parts of solid product. The solid was dissolved in 40 parts of ethanol and the solution was heated to reflux. Twenty-five parts of concentrated HCl was added and the solution was refluxed for one hour. The ethanol was removed by vacuum distillation to yield 15.08 parts of yellow solid. The solid was neutralized with six parts of sodium bicarbonate in 200 parts of water, extracted three times with methylene chloride, dried over anhydrous sodium sulfate, filtered, and the methylene chloride removed by vacuum distillation to yield 694 parts of solid. The solid, a mixture of 4-trifluoromethylaniline and 2-fluoro-4-trifluoromethylaniline, was dissolved in 133 parts of methylene chloride and 1.86 parts of phosphoric acid was added slowly, with the resultant formation of a precipitate. The mixture was then filtered, the methylene chloride removed and the remaining filtrate distilled to yield 4.06 parts of 2-fluoro-4-trifluoromethylaniline.

EXAMPLE 27

Fluorination of N-Phenylmethanesulfonamide

A solution of 8.55 parts of N-phenylmethanesulfonamide in 75 parts of trifluoroacetic acid was cooled to 0° C. and fluoroxytrifluoromethane was bubbled into the solution for one hour at a rate of 5.39 parts/hour. The solution was then degassed and the solvent removed. Analysis of the reaction product by liquid chromatographic techniques indicated 60% N-(2-fluorophenyl)methanesulfonamide, 18% N-(4-fluorophenyl)methanesulfonamide, 4% N-(2,4-difluorophenyl)methanesulfonamide) and 0.4% N-(2,6-difluorophenyl)methanesulfonamide at 88% conversion.

EXAMPLE 28

Fluorination of N-phenylmethanesulfonamide

The procedure of Example 26 was repeated except that in place of the fluoroxytrifluoromethane, there was added bis-(fluoroxy)difluoromethane at a rate of 2.40 parts per hour for one hour. Analysis of the reaction product by liquid chromatographic techniques indicated 38% N-(2-fluorophenyl)methanesulfonamide, 12% N-(4-fluorophenyl)methanesulfonamide, 10% N-(2,4-difluorophenyl)methanesulfonamide and 1% N-(2,6-difluorophenyl)methanesulfonamide at 97% conversion.

EXAMPLE 29

Fluorination of N-phenyl-1,1,1-trifluoromethanesulfonamide with fluoroxytrifluoromethane A solution of 11.25 parts of N-phenyl-1,1,1-trifluoromethane sulfonamide in 750 parts of trifluoroacetic acid was cooled to 0° C. and fluoroxytrifluoromethane was added for 1.5 hours at a rate of 5.39 parts per hour. The solution was then degassed and the solvent removed. Analysis of the reaction product by liquid chromatographic techniques indicated 44% N-(2-fluorophenyl)1,1,1-trifluoromethanesulfonamide, 38% N-(4-fluorophenyl)1,1,1-trifluoromethanesulfonamide, and 6% N-(2,4-difluorophenyl)1,1,1-trifluoromethanesulfonamide at 94% conversion.

EXAMPLE 30

Fluorination of N-phenyl-1,1,1-trifluoromethanesulfonamide with bis-(fluoroxy)-difluoromethane A solution of 11.36 parts of N-phenyl-1,1,1-trifluoromethanesulfonamide in 750 parts of trifluoroacetic acid was cooled to 0° C. and bis-(fluoroxy)difluoromethane was added for 1.67 hours at a rate of 2.59 parts per hour. The solution was degassed and the solvent removed. Analysis of the reaction product by liquid chromatographic techniques indicated 37% N-(2-fluorophenyl)-1,1,1-trifluoromethanesulfonamide, 29% N-(4-fluorophenyl)-1,1,1-trifluoromethanesulfonamide, and 12% N-(2,4-difluorophenyl)-1,1,1-trifluoromethanesulfonamide at 98% conversion.

EXAMPLE 31

Fluorination of 4-Cyanoacetanilide with Fluoroxytrifluoromethane

8 Parts of 4-cyanoacetanilide was dissolved in 680 parts of acetic acid. The solution was stirred at room temperature while 5.5 parts of fluoroxytrifluoromethane was added at a rate of 6 parts per hour for 0.92 hours. Gas chromatographic analysis of the product indicated 23.7% unreacted 4-cyanoacetanilide, 41.1% 2-fluoro-4-cyanoacetanilide and 2.8% 2,6-difluoro-4-cyanoacetanilide.

EXAMPLE 32

Fluorination of 4-Nitroacetanilide with Fluoroxytrifluoromethane

9 Parts of 4-nitroacetanilide was dissolved in 630 parts of acetic acid. The solution was stirred at room temperature while 5.49 parts of fluoroxytrifluoromethane was added over a period of one hour. Analysis of the product by gas chromatographic techniques indicated 17.6% unreacted 4-nitroacetanilide, 67.6% 2-fluoro-4-nitroacetanilide, and 4.5% of 2,6-difluoro-4-nitroacetanilide.

EXAMPLE 33

Fluorination of 4-methylacetanilide with fluoroxytrifluoromethane

A solution of 7.5 parts of 4-methylacetanilide in 315 parts of acetic acid was stirred at room temperature while 5.84 parts of fluoroxytrifluoromethane was added over a one hour period. Analysis of the reaction product by gas chromatographic techniques indicated 29.7% unreacted 4-methylacetanilide, and 33.8% of 2-fluoro-4-methylacetanilide.

EXAMPLE 34

Fluorination of N-phenylphthalimide

A solution of 150 parts of N-phenylphthalimide in 11,390 parts of nitromethane was maintained at about 25° C. while 94 parts of fluoroxytrifluoromethane was bubbled into the solution over a period of 5.5 hours. The solvent was then removed by vacuum distillation. Analysis of the crude reaction product by gas chromatography and F-19 nuclear magnetic resonance indicated 25% unreacted N-phenylphthalimide, 23% N-(2-fluorophenyl)phthalimide, 26% N-(4-fluorophenyl)phthalimide, 1% of N-(2,4-difluorophenyl) and N-(2,6-difluorophenyl)phthalimides.

EXAMPLE 35

Fluorination of N-methylacetanilide

A solution of 74.5 parts of N-methylacetanilide in 14,850 parts of chloroform was maintained at about 0° C. for a period of two hours while 96.5 parts of fluoroxytrifluoromethane was bubbled into the solution. The reaction product was dried over anhydrous $Na_2SO_4$, filtered and evaporated to yield 84 parts of brown liquid. Analysis of this reaction product by C-13 nuclear magnetic resonance indicated 64% unreacted N-methylacetanilide, 21% N-methyl-2-fluoroacetanilide and 15% N-methyl-4-fluoroacetanilide.

EXAMPLE 36

Fluorination of 4-trifluoromethylacetanilide with excess of fluorinating agent.

A solution of 1.15 parts of 4-trifluoromethylacetanilide in 82 parts of trifluoroacetic acid was maintained at about 0° C. while 2.8 parts of fluoroxytrifluoromethane was introduced over a period of about 8.5 hours. The proportions of reactants represented approximately a 5 molar excess of fluoroxytrifluoromethane. The solvent was removed and the reaction product analyzed by gas chromatography. Analysis indicated a 74% yield of 2-fluoro-4-trifluoromethylacetanilide, at a 90% conversion.

A series of fluorination reactions were carried out in accordance with this invention to determine the effect of solvent type on the ortho-para ratio obtained from the reaction of fluoroxytrifluoromethane or bis(fluoroxy)difluoromethane with various N-substituted anilines in various solvents. The ranges of ortho-para ratios (o/p) obtained are set forth according to solvent type and N-substituent, in Table 2, below.

TABLE 2

Effect of Solvent Type on O/P in the Fluorination Reaction of N—Substituted Anilines with FTM and (BDM)*

| Solvent Type | N—Substituent | | | |
|---|---|---|---|---|
| | $-\overset{\overset{O}{\|\|}}{C}-CH_3$ | $-\overset{\overset{O}{\|\|}}{C}-CF_3$ | $-\overset{\overset{O}{\|\|}}{\underset{\underset{O}{\|\|}}{S}}-CH_3$ | $-\overset{\overset{O}{\|\|}}{\underset{\underset{O}{\|\|}}{S}}-CF_3$ |
| Aprotic, non-polar $CHCl_3$, $CCl_4$ | 2.2–2.8 (2.4–5.0) | 2.9–6.7 (3.4–6.4) | 3.7–8.8 (3.3–6.0) | 2.0–3.5 |
| Aprotic, polar $CH_2Cl_2$, $CH_3-\overset{\overset{O}{\|\|}}{C}-CH_3$ $CH_3NO_2$, $CH_3CN$ | 1.7–2.0 (1.5–3.6) | 1.5–2.4 (1.8–2.8) | 1.6–2.6 (1.5–2.3) | 1.0–1.3 |
| Protic, polar $CH_3OH$, $(CH_3)_3COH$ $HCO_2H$, $CH_3CO_2H$, $CF_3CO_2H$ | 1.5–2.0 (2.0–2.6) | 1.0–2.0 (1.0–2.0) | 2.6–3.7 (2.2–3.0) | 0.7–1.5 |

*Parenthesis ( ) indicates data based on use of BDM as fluorinating agent.

What is claimed is:

1. A process for the preparation of 2-fluoro-4-trifluoromethylaniline which comprises:
   (A) reacting 4-trifluoromethyl-acetanilide with fluoroxytrifluoromethane to form 2-fluoro-4-trifluoromethylacetanilide
   (B) hydrolyzing the 2-fluoro-4-trifluoromethylacetanilide to form the 2-fluoro-4-trifluoromethyl aniline product which contains a quantity of 4-trifluoromethylaniline,
   (C) treating the 2-fluoro-4-trifluoromethylaniline product by acidification with phosphoric acid to form a precipitate containing the 4-trifluoromethylaniline, and
   (D) separating the precipitate from the liquid containing 2-fluoro-4-trifluoromethylaniline.

* * * * *